(12) United States Patent
Shino et al.

(10) Patent No.: US 9,999,495 B2
(45) Date of Patent: Jun. 19, 2018

(54) LIGAMENT RECONSTRUCTION FIXATION SYSTEM

(71) Applicants: Smith & Nephew, Inc., Memphis, TN (US); Konsei Shino, Osaka (JP)

(72) Inventors: Konsei Shino, Osaka (JP); Stephen Santangelo, Sturbridge, MA (US); Jeffrey Wyman, Naples, FL (US)

(73) Assignee: Smith & Nephew, Inc., Memphis, TN (US)

( * ) Notice: Subject to any disclaimer, the term of this patent is extended or adjusted under 35 U.S.C. 154(b) by 0 days. days.

(21) Appl. No.: 15/423,993

(22) Filed: Feb. 3, 2017

(65) Prior Publication Data

US 2017/0143471 A1    May 25, 2017

Related U.S. Application Data

(62) Division of application No. 14/409,111, filed as application No. PCT/US2013/047784 on Jun. 26, 2013, now Pat. No. 9,629,706.
(Continued)

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/044* (2013.01); *A61B 2017/0414* (2013.01); *A61B 2017/0445* (2013.01); *A61B 2017/0464* (2013.01); *A61F 2002/087* (2013.01); *A61F 2002/0817* (2013.01); *A61F 2002/0829* (2013.01); *A61F 2002/0841* (2013.01); *A61F 2002/0847* (2013.01); *A61F 2002/0852* (2013.01);
(Continued)

(58) Field of Classification Search
CPC ............ A61F 2/0811; A61F 2002/0823; A61F 2002/0829; A61F 2002/0852
See application file for complete search history.

(56) References Cited

U.S. PATENT DOCUMENTS 6,517,542 B1 *   2/2003   Papay ................ A61B 17/0401
                                                                606/232
2002/0156476 A1   10/2002   Wilford et al.
(Continued)

FOREIGN PATENT DOCUMENTS

WO    2010121302 A1    10/2010
WO    2012056384 A2    5/2012

OTHER PUBLICATIONS

Office Action from related Japanese Application No. 2015-520421 dated Apr. 10, 2017.
(Continued)

*Primary Examiner* — Thomas J Sweet
*Assistant Examiner* — Daniel Bissing
(74) *Attorney, Agent, or Firm* — Burns & Levinson, LLP; Joseph M. Maraia

(57) ABSTRACT

The present disclosure relates to an assembly for fixing a ligament in bone. The assembly includes a suspension member and an implant having a mechanism for fixedly receiving the suspension member and at least partially suspending the suspension member and the received bone graft within the implant, allowing for bony in-growth. A method of fixing a ligament in bone is also disclosed.

8 Claims, 4 Drawing Sheets

Related U.S. Application Data

(60) Provisional application No. 61/664,867, filed on Jun. 27, 2012.

(52) U.S. Cl.
CPC ............... *A61F 2002/0858* (2013.01); *A61F 2002/0882* (2013.01)

(56) References Cited

U.S. PATENT DOCUMENTS

| | | | |
|---|---|---|---|
| 2012/0041496 A1* | 2/2012 | Walker | A61F 2/0811 606/321 |
| 2012/0095470 A1 | 4/2012 | Kaiser et al. | |

OTHER PUBLICATIONS

Office Action from related Australian Application No. 2013280421 dated Feb. 3, 2017.

* cited by examiner

LIGAMENT RECONSTRUCTION FIXATION SYSTEM

CROSS-REFERENCE TO RELATED APPLICATIONS

This application is a divisional of co-pending U.S. patent application Ser. No. 14/409,111, filed Dec. 18, 2014, entitled LIGAMENT RECONSTRUCTION FIXATION SYSTEM, which in turn is the U.S. national phase entry under 35 U.S.C. § 371 of International Application No. PCT/US13/47784, filed Jun. 26, 2013, which in turn claims priority to and benefit of U.S. Provisional Application No. 61/664,867, filed Jun. 27, 2012, the entire contents of which are hereby incorporated by reference herein for all purposes.

FIELD OF TECHNOLOGY

The present disclosure relates to the surgical repair of tissue and, more specifically, devices and methods for ligament reconstruction.

RELATED ART

Fibrous tissues, such as ligaments and tendons, can detach from bone. Suture anchors are commonly used to attach soft and hard tissue to bone. Typically, a suture anchor is implanted into a drilled bore in bone mass. One or more sutures with attached needles are connected to the suture anchor. The suture is passed through the tissue and subsequently tied to secure the tissue to the bone.

Many ligament reconstruction fixation devices such as endobutton or suspension pins have been identified as potential solutions to fix ligaments during surgical reconstruction. Some of the surgical procedures used with these devices are inefficient and some of the devices do not allow optimal contact of the graft tissue or scaffold with the bone.

SUMMARY OF THE INVENTION

In one aspect, the present disclosure relates to an assembly for fixing a ligament in bone. The assembly includes a suspension member having a first end for receiving a bone graft, and an implant having a mechanism for fixedly receiving a second end of the suspension member and at least partially suspending the suspension member within the implant, allowing for bony in-growth. Such an assembly allows a tissue graft to be suspended within a bone tunnel and eventually to contact the bone tunnel walls through a full 360 degrees which promotes faster healing. In a further embodiment, implant is a fenestrated implant, and the second end of the suspension member includes a suture loop hook having at least two hook portions, and the mechanism for fixedly receiving the second end of the suspension member includes apertures in the fenestrated implant. In another embodiment, fenestrated implant is a Healicoil suture anchor. In yet another embodiment, the assembly further includes a guide pin having an attachment site for the suspension member and wherein the guide pin is threaded through the implant. In a further embodiment, the implant is a bioabsorbable material.

In another embodiment, a size of the implant is proportional to a graft size and the pilot hole such that implant fixation and graft to socket contact is maximized. In other embodiments the implant can be a screw implant or a ribbed plug implant, and the second end of the suspension member includes at least two J-lock members and the mechanism for fixedly receiving the second end of the suspension member can be J-lock retainer groves in the implant or the second end of the suspension member includes at least two snap fit tabs and the mechanism for fixedly receiving the second end of the suspension member includes snap fit groves in the implant.

One method for ligament reconstruction as disclosed herein includes inserting an implant into an aperture, attaching a graft to a first end of a suspension member, securing a second end of the suspension member to a guide pin, positioning the guide pin to align the suspension member with the aperture and engaging the suspension member with the implant, thereby at least partially suspending the graft within the aperture. In one embodiment, this technique creates a ligament to bone/anterior cruciate ligament (ACL) femoral fixation system which secures the graft, tissue or scaffold into a prepared bone socket (e.g., bone tunnel) while allowing for 360 degree contact of the graft or scaffold with the bone socket that is created. In a further embodiment, the pilot hole is drilled to receive the implant, and in another embodiment, drilling the pilot hole and inserting the implant is performed in a single operation.

In a further embodiment, implant fixation and graft to socket contact are maximized by sizing the implant proportionally to a size of the graft and a size of the pilot hole. In another embodiment, engaging the suspension member with the implant includes hooking at least two hooks portions disposed on the second end of the suspension member to apertures in the fenestrated implant. In a further embodiment, engaging the suspension member with the implant includes locking at least two suspension member J-lock members into corresponding J-lock retainer grooves in the implant.

A kit for ligament reconstruction includes a suspension member having a first end for securing a bone graft, a implant having a mechanism for fixedly receiving a second end of the suspension member and suspending the suspension member and received bone graft within the implant, the implant allowing for bony in-growth and an insertion device configured to assist with implanting the implant into a body.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses. As disclosed herein, an assembly for fixing a ligament in bone includes an implant and matching suspension member which is attached to the implant during ligament reconstruction procedures. This assembly suspends a bone graft connected to the suspension member distally from the implant which may be attached to a drill via a guide pin and inserted during pilot hole placement.

Figure 1:
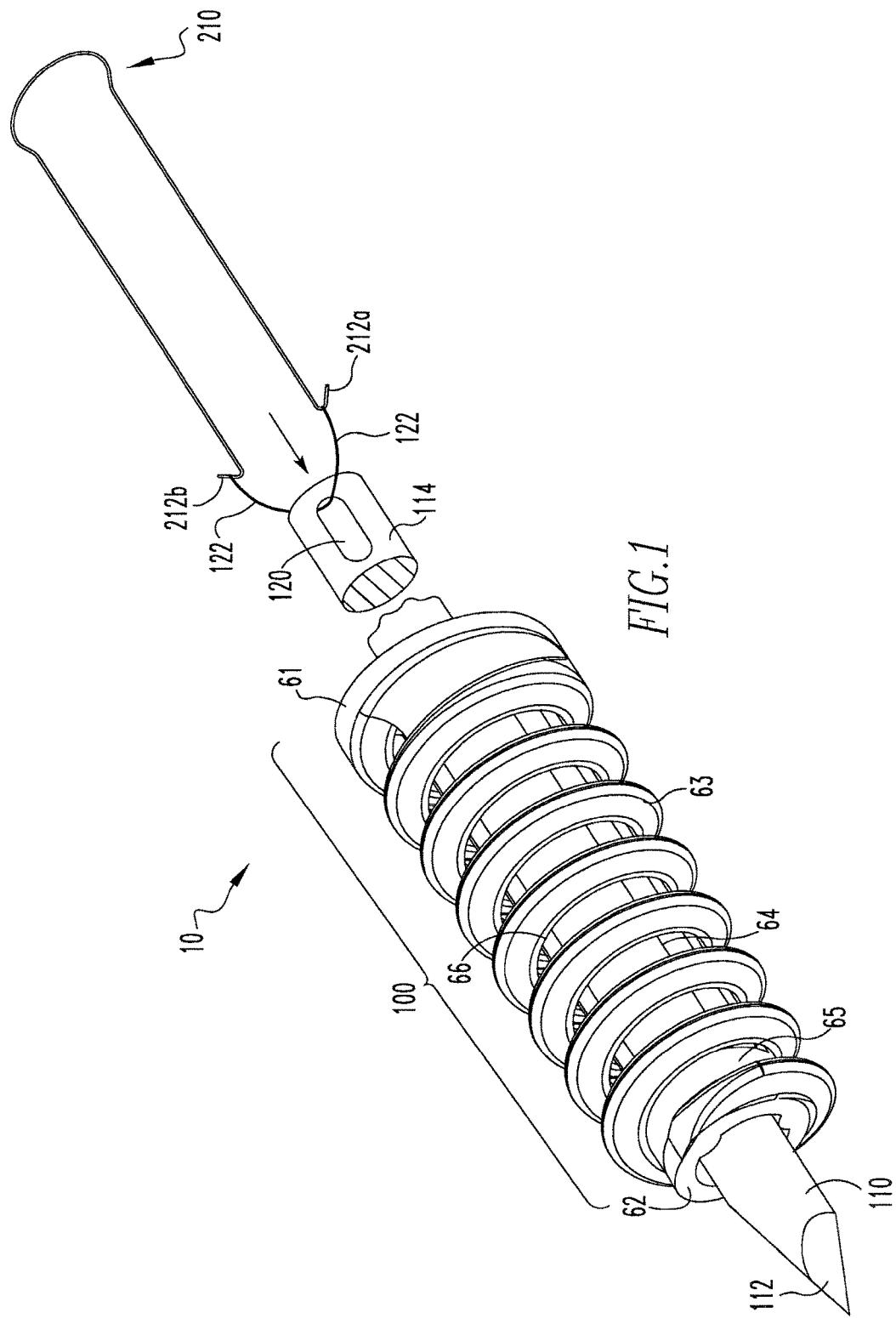
FIG. 1 shows a perspective view of the implant and drill guide of the present disclosure.

Now referring to FIG. 1, an exemplary assembly 10 for fixing a ligament in bone includes an implant 100 which is inserted, for example, in a bone tunnel in a femoral socket. The implant 100 includes a distal end 61, a proximal end 62, a coil portion 63 (also referred to as a thread) and apertures 64-66. In one embodiment, prior to insertion, the implant is assembled on a drill guide wire 110 (also referred to as a guide pin 110). The drill guide wire 110 can include an attachment site 120 which is connected to a suspension member 210, a drilling end 112, and a distal end 114. The suspension member 210 includes a first end 214 and a second end, here shown as hook portions 212a and 212b (commonly referred to as hook portions 212). In one embodiment the suspension member 210 is pulled through the implant the hook portions 212a and 212b are engaged with the locking mechanism of the implant 100. In one embodiment, the locking mechanism includes the apertures 64-66 and the coil portion 63 interfacing with hook portions 212. In this embodiment the hook portions 212 contact and hook around the coil portion 63 through the apertures 64-66. In other embodiments, the suspension member 210 is connected to the implant 100 with a J-lock connection or a snap fit. In one embodiment the suspension member 210 is connected to the attachment site 120 using a suture 122 attached to hook portions 212. In other embodiments, the suspension member 210 is inserted without the drill guide 110 using a device to push the suspension member 210 into position which then locks into the implant 100.

There are several methods to insert the implant 100. In one embodiment a pilot hole is drilled using the drill guide wire 110 followed by a cannulated drill to form the bone tunnel. In these embodiments, drilling of the bone tunnel and insertion of the implant is performed in a single operation. In one embodiment the implant is similar to a Smith & Nephew HEALICOIL™ Suture Anchor which differs from conventional solid-core implants by eliminating the inner diameter material. This allows for the bone to interdigitate within the anchor thread profile, providing excellent fixation security. In one embodiment the Healicoil™ type implant is preloaded on a drill. Specifically, according to one technique for fixing the implant, the drill and implant are preloaded and inserted over a guide pin 110 that was previously placed. The implant 100 and drill work as one to create the pilot hole and also insert the implant into position. Once the implant 100 is positioned the guide pin 110 is used to secure the suspension member 210 (e.g., suture clip) within the implant and to suspend the bone graft attached to suture clip 210 in the pilot hole adjacent to the distal end 61 of the implant or partially inside the implant in other embodiments. Other methods of inserting the implant 100 includes the use of special purpose insertion instruments. The implant 100 can also be inserted in a conventionally drilled bone tunnel.

In another embodiment, the implant 100 is biocompatible with tissue and is a made from a bioabsorbable material (i.e., able to degrade over time in a biological environment, such as the human body, to compounds that are removed during normal metabolic processes). In another embodiment, the implant 100 can be sized proportionally to the bone graft size and the pilot hole such that implant fixation and graft to socket contact is maximized. The size of the implant 100 can vary to fit the bone tunnel, for example, from 4.5 mm to 13.0 mm. The assembly 10 and techniques described herein can be used for boney grafts or soft tissue grafts.

Figure 2:
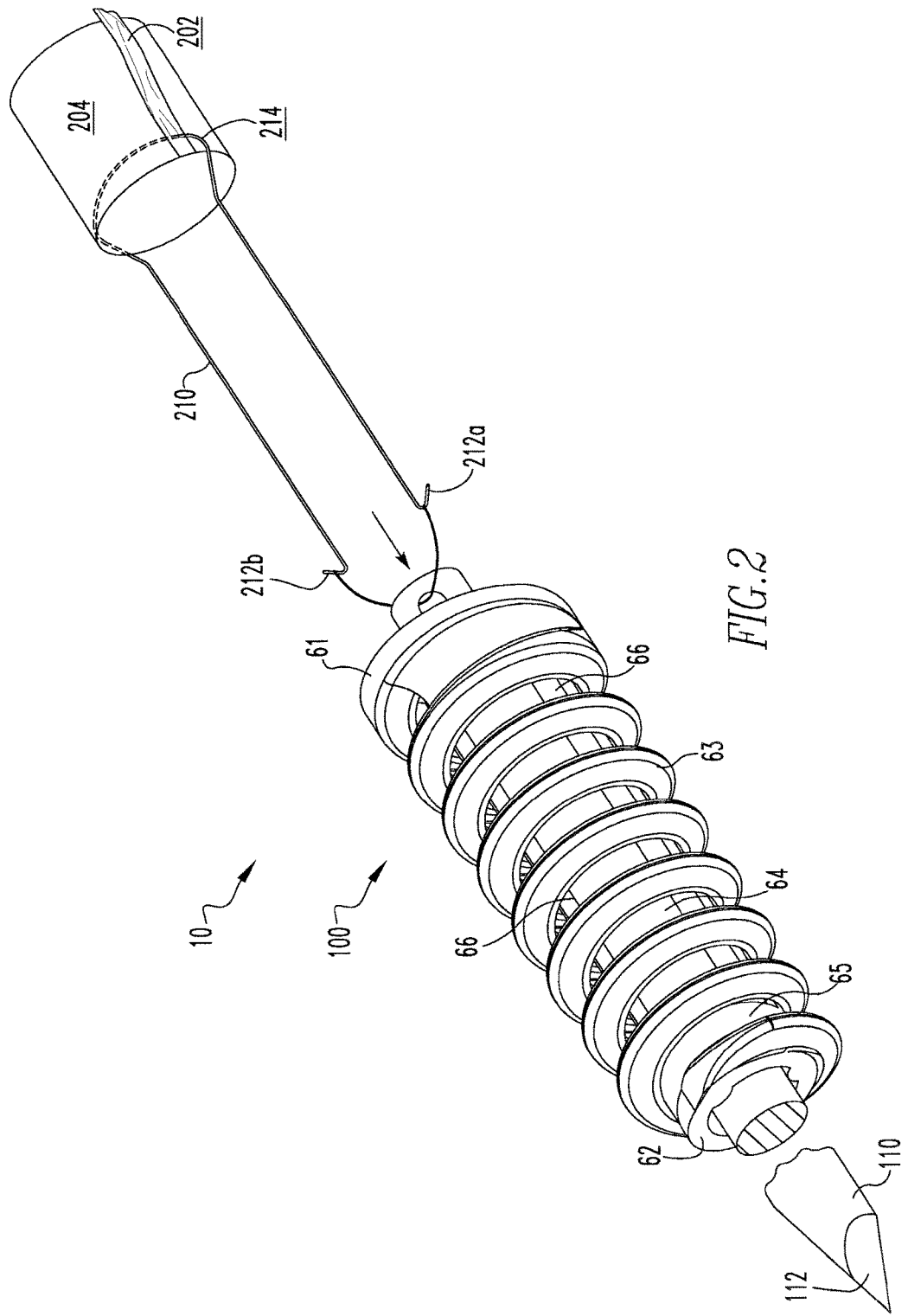
FIG. 2 shows an exploded view of an assembly of the present disclosure for fixing a ligament in bone.

FIG. 2 shows one embodiment of an assembly 10 for fixing a ligament in bone. The assembly 10 includes a suspension member 210 having a first end 214 and a second end, here shown as hook portions 212). A ligament 202 is attached to a bone graft 204 (also referred to as a bone to bone (BTB) graft 204). The first end 214 of the suspension member 210 receives the BTB graft 204. In one embodiment, the BTB graft 204 is attached to the first end 214 of the suspension member 210 using a suture or similar material In other embodiments, the suspension member 210 is attached to the BTB graft by either a suture through the bone block, a screw into the bone block, tape, or passed directly through the BTB graft 204 and secured. If the graft is a soft tissue graft, the graft 204 can be folded over or looped around the suspension member 210. If the graft is a boney graft as shown is FIG. 2, the suspension member 210 can be sutured to the graft, or passed directly through the graft 204.

After the implant 100, here a fenestrated implant, is fixed in the bone tunnel 304 (FIG. 3) of a femur socket 302 (FIG. 3), the second end of the suspension member is secured to the guide pin 110. The guide pin 110 is positioned to align the suspension member with the pilot hole and using the guide pin 110 and the suspension member 210 is engaged with the implant 100, thereby at least partially suspending the graft 204 within the bone tunnel from the implant 100. In some embodiments the graft 204 can be at least partially suspended within the implant 100.

In one embodiment the suspension member 210 is a suture loop hook spring having a first end 214 for receiving the BTB graft 204 and the implant 100 is a fenestrated implant, for example a Healicoil™ suture anchor, having a mechanism for fixedly receiving a second end of the suspension member. In this embodiment, the locking mechanism is provided by the hook portions 212a and 212b of the suture loop hook spring 210 engaging with apertures in fenestrated implant 100 in order to suspend the suture loop hook spring 210 and received bone graft 204 within the implant and bone tunnel 304, respectively. In this embodiment, the suture loop hook spring 210 is pulled to the distal end 62 of the implant 100 and "ratchets" across the apertures 64-66 and 66 and coil 63 until the hook portions lock in place once the desired position and tension has been reached.

With this arrangement the assembly 10 for fixing a ligament in bone allows for bony in-growth within the fenestrated implant 100, the suture loop hook spring 210 and the received bone graft 204. In this embodiment, the suspension member 210, here a the suture loop hook spring, provides both a damping feature for the assembly 10 and spring tension on the hook portions 212a and 212b when engaged with apertures in the fenestrated implant 100. It is understood that the suspension member 210 can include additional hook portions 212 and can use other mechanisms for attachment to the implant 100 including but not limited to J-lock connections (described below in conjunction with FIGS. 4A-4C), snap fit tabs, threads, wings and detents. In one embodiment, the suspension member 210 is metal and in another embodiment the suspension member 210 is made from polyetheretherketone (PEEK), which is similar to plastic and has a modulus of elasticity similar to bone.

Figure 3:
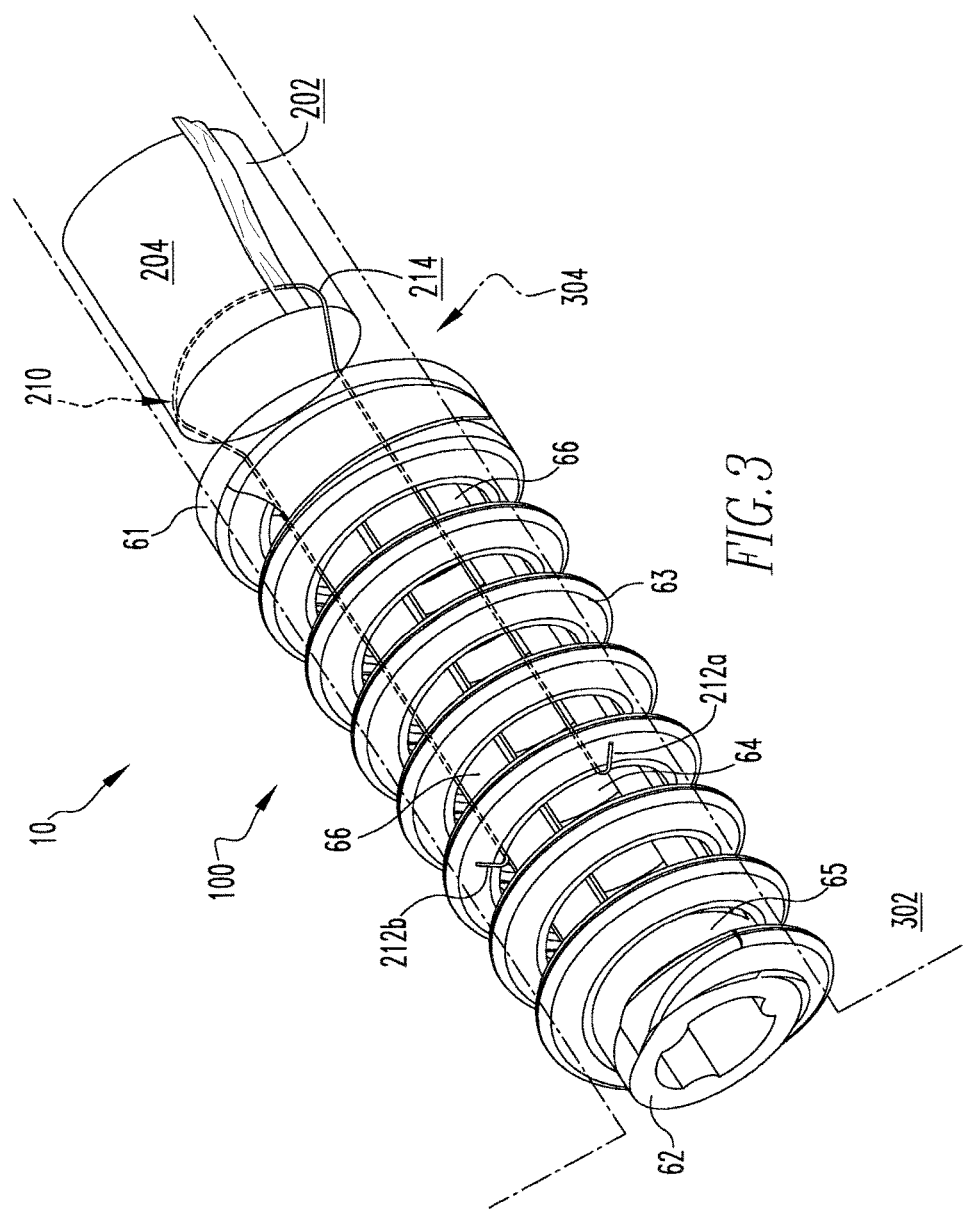
FIG. 3 shows the assembly of FIG. 2 after insertion and suspension in a bone tunnel of a femoral socket.

Now referring to FIG. 3, the assembly 10 is shown within a bone tunnel 304 of a femoral socket 302. The BTB graft 204 is attached to the suspension member 210 and is suspended from the implant 100 inserted in to the femur. In this embodiment, the graft is attached to the suspension member 210 which is suspended at least partially within the implant 100. Here, the implant 100 was attached to a drill and inserted during pilot hole placement. In this embodiment, the implant 100 is a fenestrated implant (also referred to as a cage screw fastener) which allows for bony in-growth and is similar in design to a Healicoil™ anchor with the addition of a mechanism for fixedly receiving an internal locking feature, here hook portions 212a and 212b hooked onto apertures in the implant 100.

Figure 4A:
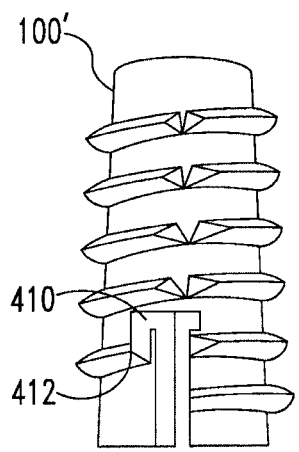
FIGS. 4A-4C show an alternate embodiment of an implant and suspension member of the present disclosure.
Figure 4B:
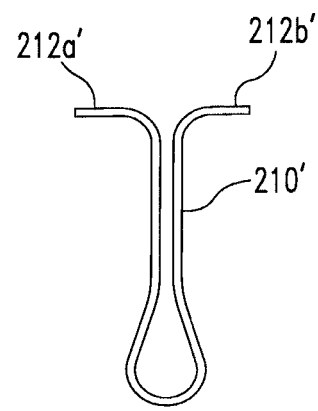
Figure 4C:
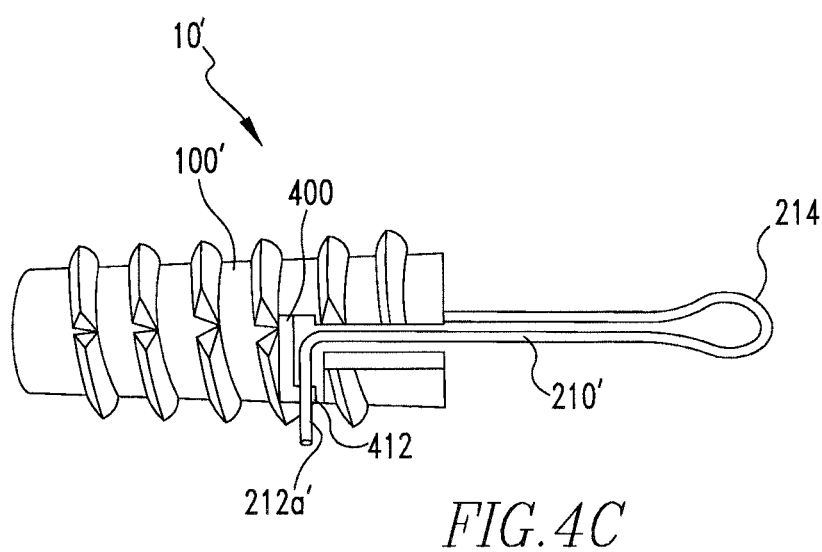

Now referring to FIGS. 4A and 4B, an alternate assembly 10' includes an implant 100' having J-lock retainer grooves 410 for receiving corresponding J-lock members 212a' and 212b' on an suspension member 210' shown as unassembled J-lock components. FIG. 4C shows the assembled components implant 100' and suspension member 210' of assembly 10' without the attached bone graft. In another embodiment, a snap fit mechanism (not shown) is used to secure a suspension member into an implant instead of the J-lock mechanism. It is understood that the implant whether a Healicoil, a screw, a screw implant, a plug implant or a ribbed plug implant can include apertures/fenestrations in the walls and can be cannulated (i.e., hollowed out to receive the suspension member).

In alternative embodiments the distance from the graft to the implant is adjusted by the length of the suspension member and the placement of the suspension member with respect to the implant, and in some embodiments the graft could be suspended at least partially within the implant or just in the bone tunnel. In other embodiments the implant can be fenestrated along its entire length, or fenestrated along part of its length. The suspension member can be a suture loop, a metal loop, a spring or a clip (i.e., any mechanism for linking the graft to the implant).

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of ligament reconstruction comprising:
   inserting an implant into a pilot hole, the implant comprising at least one open helical coil screw thread having a cannulation defining an internal volume extending a length of the implant, the cannulation communicating with a region exterior to the at least one open helical coil screw thread through apertures between turns of the at least one open helical coil screw thread;
   attaching a graft to a first end of a suspension member, the suspension member comprising a length of flexible material, the first end of the suspension member defining a loop for receiving the graft and a second end of the suspension member having at least two attachment portions;
   securing the at least two attachment portions of the second end of the suspension member to a guide pin;
   positioning the guide pin within the internal volume of the implant to align the suspension member with the pilot hole; and
   engaging the suspension member with the implant, thereby at least partially suspending the graft within the implant;
   wherein the at least two attachment portions are at least two hook portions, and engaging the suspension member with the implant comprises hooking the at least two hooks portions to the apertures in the implant.

2. The method of claim 1 further comprising drilling the pilot hole to receive the implant.

3. The method of claim 2 wherein drilling the pilot hole and inserting the implant are performed in a single operation.

4. The method of claim 1 further comprising maximizing implant fixation and graft to socket contact by sizing the implant proportionally to a size of the graft and a size of the pilot hole.

5. The method of claim 1, wherein the implant comprises a bioabsorbable material.

6. The method of claim 1, wherein inserting the implant into the pilot hole comprises inserting the implant with a delivery device.

7. A method of ligament reconstruction comprising:
   inserting an implant into a pilot hole, the implant comprising at least one open helical coil screw thread having a cannulation defining an internal volume extending a length of the implant, the cannulation communicating with a region exterior to the at least one open helical coil screw thread through apertures between turns of the at least one open helical coil screw thread;
   attaching a graft to a first end of a suspension member, the suspension member comprising a length of flexible material, the first end of the suspension member defining a loop for receiving the graft and a second end of the suspension member having at least two attachment portions;
   securing the at least two attachment portions of the second end of the suspension member to a guide pin;
   positioning the guide pin within the internal volume of the implant to align the suspension member with the pilot hole; and
   engaging the suspension member with the implant, thereby at least partially suspending the graft within the implant;
   wherein the at least two attachment portions are at least two J-lock members, and engaging the suspension member with the implant comprises locking the at least two J-lock members into corresponding J-lock retainer grooves in the implant.

8. A method of ligament reconstruction comprising:
   inserting an implant into a pilot hole, the implant comprising at least one open helical coil screw thread having a cannulation defining an internal volume extending a length of the implant, the cannulation communicating with a region exterior to the at least one open helical coil screw thread through apertures between turns of the at least one open helical coil screw thread;
   attaching a graft to a first end of a suspension member, the suspension member comprising a length of flexible material, the first end of the suspension member defining a loop for receiving the graft and a second end of the suspension member having at least two attachment portions;
   securing the at least two attachment portions of the second end of the suspension member to a guide pin;
   positioning the guide pin within the internal volume of the implant to align the suspension member with the pilot hole; and engaging the suspension member with the implant, thereby at least partially suspending the graft within the implant;

wherein the at least two attachment portions are at least two snap fit tabs, and engaging the suspension member with the implant comprises securing the at least two snap fit tabs into corresponding snap fit grooves in the implant.

* * * * *